US012622671B2

(12) United States Patent
Defreitas et al.

(10) Patent No.: US 12,622,671 B2
(45) Date of Patent: May 12, 2026

(54) MULTI-POSITION ULTRASOUND SYSTEM

(71) Applicant: HOLOGIC, INC., Marlborough, MA (US)

(72) Inventors: Kenneth F. Defreitas, Patterson, NY (US); Ian Shaw, Swampscott, MA (US); Kenneth Brooks, Marlborough, MA (US); Jay A. Stein, Boston, MA (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 18/497,053

(22) Filed: Oct. 30, 2023

(65) Prior Publication Data

US 2024/0164744 A1    May 23, 2024

Related U.S. Application Data

(63) Continuation of application No. 17/254,160, filed as application No. PCT/US2019/038430 on Jun. 21, 2019, now Pat. No. 11,832,989.

(60) Provisional application No. 62/688,889, filed on Jun. 22, 2018.

(51) Int. Cl.
*A61B 8/00* (2006.01)
*A61B 8/08* (2006.01)

(52) U.S. Cl.
CPC ............ *A61B 8/403* (2013.01); *A61B 8/0825* (2013.01); *A61B 8/406* (2013.01); *A61B 8/4218* (2013.01); *A61B 8/4461* (2013.01); *A61B 8/54* (2013.01)

(58) Field of Classification Search
CPC ....... A61B 8/403; A61B 8/0825; A61B 8/406; A61B 8/4218; A61B 8/4461; A61B 8/54; A61B 8/42; A61B 8/4209
See application file for complete search history.

(56) References Cited

U.S. PATENT DOCUMENTS

| | | |
|---|---|---|
| 5,474,072 A | 12/1995 | Shmulewitz |
| 6,161,034 A | 12/2000 | Burbank et al. |
| 6,228,055 B1 | 5/2001 | Foerster |
| 6,234,177 B1 | 5/2001 | Barsch |
| 6,436,120 B1 | 8/2002 | Meglin |
| 6,459,925 B1 | 10/2002 | Nields et al. |
| 6,574,499 B1 | 6/2003 | Dines et al. |

(Continued)

FOREIGN PATENT DOCUMENTS

| | | |
|---|---|---|
| CN | 1672032 A | 9/2005 |
| CN | 1802125 A | 7/2006 |

(Continued)

OTHER PUBLICATIONS

European Communication pursuant to Article 94(3) EPC in Application 19737388.9, mailed Mar. 20, 2023, 6 pages.

(Continued)

*Primary Examiner* — Kaitlyn E Sebastian
(74) *Attorney, Agent, or Firm* — Merchant & Gould P.C.

(57) ABSTRACT

A compression assembly is coupled to the gantry of an ultrasound breast imaging system. The compression assembly includes a pair of compression paddles mounted on a positioning track. Each compression paddle houses a transducer and has a compression material surface for patient contact. A motor moves the compression paddles along the positioning track to immobilize the breast for ultrasound imaging.

19 Claims, 12 Drawing Sheets

(56) References Cited

U.S. PATENT DOCUMENTS

| | | | |
|---|---|---|---|
| 8,401,622 | B2 | 3/2013 | Talpade et al. |
| 9,433,390 | B2 | 9/2016 | Nathaniel |
| 9,669,113 | B1 | 6/2017 | Sirimanne et al. |
| 9,713,437 | B2 | 7/2017 | Fullerton |
| 11,234,772 | B2 | 2/2022 | Laviola |
| 11,432,883 | B2 | 9/2022 | Laviola |
| 11,464,585 | B2 | 10/2022 | Laviola |
| 11,832,989 | B2 | 12/2023 | DeFreitas |
| 11,937,886 | B2 | 3/2024 | Laviola |
| 12,029,503 | B2 | 7/2024 | Laviola |
| 2002/0151797 | A1 | 10/2002 | Montegrande |
| 2003/0192557 | A1 | 10/2003 | Krag et al. |
| 2003/0228044 | A1 | 12/2003 | Gopalasamy |
| 2004/0034307 | A1 | 2/2004 | Johnson |
| 2004/0181152 | A1* | 9/2004 | Zhang ................ G01S 15/8938 |
| | | | 600/437 |
| 2004/0236211 | A1 | 11/2004 | Burbank |
| 2005/0152588 | A1 | 7/2005 | Yoshida et al. |
| 2005/0215874 | A1 | 9/2005 | Wang et al. |
| 2006/0009696 | A1 | 1/2006 | Hanover et al. |
| 2006/0030847 | A1 | 2/2006 | McGuckin, Jr. |
| 2007/0038085 | A1 | 2/2007 | Zhang et al. |
| 2007/0093726 | A1 | 4/2007 | Leopold et al. |
| 2007/0239016 | A1 | 10/2007 | Fisher |
| 2007/0250102 | A1 | 10/2007 | Makower et al. |
| 2008/0097199 | A1 | 4/2008 | Mullen |
| 2008/0249415 | A1 | 10/2008 | Okamura et al. |
| 2008/0269613 | A1* | 10/2008 | Summers ............... A61B 8/483 |
| | | | 600/459 |
| 2008/0281190 | A1 | 11/2008 | Petcavich et al. |
| 2009/0003519 | A1 | 1/2009 | DeFreitas et al. |
| 2009/0131825 | A1 | 5/2009 | Burbank et al. |
| 2010/0022871 | A1 | 1/2010 | De Beni et al. |
| 2010/0030072 | A1 | 2/2010 | Casanova et al. |
| 2010/0063392 | A1 | 3/2010 | Nishina |
| 2010/0204570 | A1 | 8/2010 | Lubock |
| 2010/0246767 | A1 | 9/2010 | Tanabe |
| 2010/0280375 | A1 | 11/2010 | Zhang et al. |
| 2010/0305430 | A1 | 12/2010 | Troessken |
| 2011/0130659 | A1 | 6/2011 | Cinquin et al. |
| 2011/0313288 | A1 | 12/2011 | Chi Sing |
| 2011/0319746 | A1 | 12/2011 | Kochba et al. |
| 2012/0265296 | A1 | 10/2012 | McNamara et al. |
| 2013/0184571 | A1 | 7/2013 | Wilkening |
| 2013/0345525 | A1 | 12/2013 | Kline |
| 2014/0309522 | A1 | 10/2014 | Fullerton et al. |
| 2014/0364728 | A1 | 12/2014 | Hashimoto |
| 2015/0005804 | A1 | 1/2015 | Franano et al. |
| 2015/0141795 | A1* | 5/2015 | Kim .................... A61B 5/0091 |
| | | | 600/407 |
| 2015/0196369 | A1 | 7/2015 | Glossop |
| 2015/0294495 | A1 | 10/2015 | Nielsen et al. |
| 2016/0081633 | A1 | 3/2016 | Stango et al. |
| 2016/0128668 | A1 | 5/2016 | Jain |
| 2016/0310760 | A1 | 10/2016 | Bharat et al. |
| 2017/0011516 | A1 | 1/2017 | Snook et al. |
| 2017/0202635 | A1 | 7/2017 | Ramos |
| 2017/0213358 | A1 | 7/2017 | Furuichi |
| 2017/0251991 | A1 | 9/2017 | Wang et al. |
| 2017/0367675 | A1* | 12/2017 | Arai ....................... A61B 6/502 |
| 2018/0055476 | A1 | 3/2018 | Pizzatola et al. |
| 2018/0103912 | A1 | 4/2018 | Canfield et al. |
| 2018/0104008 | A1 | 4/2018 | Dickhans |
| 2018/0140260 | A1 | 5/2018 | Taguchi |
| 2018/0184999 | A1* | 7/2018 | Davis .................... A61B 8/403 |
| 2018/0214106 | A1 | 8/2018 | Wang et al. |
| 2019/0110858 | A1 | 4/2019 | Stubbs |
| 2019/0201160 | A1 | 7/2019 | Hornscheidt |
| 2021/0169579 | A1 | 6/2021 | Laviola |
| 2022/0039878 | A1 | 2/2022 | Laviola |
| 2022/0039879 | A1 | 2/2022 | Laviola |
| 2022/0061930 | A1 | 3/2022 | Laviola |
| 2022/0061931 | A1 | 3/2022 | Laviola |
| 2022/0071714 | A1 | 3/2022 | Laviola |
| 2022/0110699 | A1 | 4/2022 | Laviola |

FOREIGN PATENT DOCUMENTS

| | | | |
|---|---|---|---|
| CN | 101951840 | A | 1/2011 |
| CN | 103547902 | A | 1/2014 |
| CN | 104540447 | A | 4/2015 |
| DE | 102013219252 | | 3/2015 |
| JP | 2002065876 | A | 3/2002 |
| JP | 2003325523 | A | 11/2003 |
| JP | 2008-272459 | | 11/2008 |
| JP | 2009-119275 | | 6/2009 |
| JP | 4418888 | B1 | 2/2010 |
| JP | 2013-94371 | | 5/2013 |
| JP | 2017176465 | | 10/2017 |
| JP | 2008-6130 | | 6/2020 |
| KR | 10-2015-0058714 | | 5/2015 |
| KR | 10-2021-0011932 | A | 2/2021 |
| WO | 01/08578 | | 2/2001 |
| WO | 2007/014292 | | 2/2007 |
| WO | 2012/048000 | | 4/2012 |
| WO | 2013/096766 | | 6/2013 |
| WO | 2013/163381 | | 10/2013 |
| WO | 2015/138795 | | 9/2015 |

OTHER PUBLICATIONS

PCT International Preliminary Report on Patentability in International Application PCT/US2019/038430, mailed Dec. 30, 2020, 9 pages.

PCT International Search Report and Written Opinion in International Application PCT/US2019/038430, mailed Oct. 22, 2019, 13 pages.

* cited by examiner

CC

MLO

FRONTAL

LATERAL

600

602c

MULTI-POSITION ULTRASOUND SYSTEM

CROSS-REFERENCE TO RELATED APPLICATIONS

This application is a continuation application of U.S. patent application Ser. No. 17/254,160, filed Dec. 18, 2020, now U.S. Pat. No. 11,832,989, which is a National Stage Application of PCT/US2019/038430, filed Jun. 21, 2019, and that claims priority to and the benefit of U.S. Provisional Patent Application No. 62/688,889, filed Jun. 22, 2018, the disclosures of which are hereby incorporated by reference herein in their entireties. To the extent appropriate, a claim of priority is made to each of the above disclosed applications.

BACKGROUND

Ultrasound breast imaging, also called ultrasound scanning or sonography, involves exposing breast tissue to high-frequency sound waves. As the sound waves reflect off different features within the breast, the reflections can be used to produce two and three dimensional images of the internal breast structure. Ultrasound images are captured in real-time and they advantageously show the structure and movement of the body's internal organs as well as blood flowing through blood vessels.

Breast ultrasound may be used as part of breast cancer diagnosis to determine whether a lump is a benign fluid filled sac (i.e., a cyst) or a solid mass potentially indicative of cancer. Ultrasound can also be used during a breast biopsy procedure to determine three dimensional coordinates of an identified tumor in order to guide a medical professional during a biopsy or aspiration procedure. Ultrasound may be used to confirm correct needle placement and also validate removal of suspect tissue.

Ultrasound imaging is recognized as a relatively low cost, safe imaging modality which provides information similar to that of conventional mammograms (and in some cases superior) for breast cancer detection without adverse effects of radiation. However the time required to perform a thorough ultrasound image capture makes the modality less desirable for breast cancer screening. During breast ultrasound examinations, an ultrasound transducer is typically manually moved over the portion of the body to be imaged. Two dimensional images are captured from various perspectives and assembled using image processing techniques known to those of skill in the art to construct a three-dimensional representation of the breast. Although the ability to manually manipulate the transducer allowed the medical professional the freedom to more thoroughly examine regions of interest during the scan, the time required to perform a complete scan could quickly accumulate.

SUMMARY

In one aspect, the technology relates to an ultrasound breast imaging system including: a gantry: and a compression assembly coupled to the gantry, the compression assembly including: a pair of compression paddles mounted on a positioning track, each compression paddle housing a transducer and having a patient contact surface including a compression material: and a motor for moving at least one of the compression paddles along the positioning track to immobilize a breast for ultrasound imaging. In an example, the compression paddle includes a housing and wherein the patient contact surface is detachable from the housing. In another example, the ultrasound breast imaging system further includes a rotatable arm coupling the compression assembly to the gantry for rotating the compression assembly to a plurality of scan perspectives for performing at least one of a cranial-caudal, mediolateral oblique, lateral, and frontal scan. In yet another example, the compression assembly further includes a positioning structure, and a support arm for each compression paddle, each support arm for pivotably coupling the associated compression paddle to the positioning structure. In still another example, the ultrasound breast imaging system further includes a user interface mounted on the gantry and including controls for controlling at least one of a position of the compression assembly and an ultrasound scan workflow.

In another example of the above aspect, the compression material is at least partially elastic. In an example, the compression material is rigid. In another example, at least one of the transducers housed in the compression paddle is configured to move along a scan path to obtain an ultrasound image. In yet another example, the ultrasound breast imaging system further includes a plurality of transducers, wherein each of the plurality of transducers is configured to move along different scan paths during ultrasound imaging. In still another example, the scan path is generally helical.

In another aspect, the technology relates to a breast ultrasound imaging system including: a gantry; an arm extending from the gantry; a paddle support structure disposed at an end of the arm opposite the gantry; a compression paddle assembly coupled to the paddle support structure, wherein the compression paddle assembly includes at least one compression element having: a paddle support arm secured to the paddle support structure; a compression paddle pivotably secured to the paddle support arm; and an ultrasound transducer disposed within the compression paddle. In an example, the paddle support structure is pivotable relative to the arm. In another example, the at least one compression element is linearly positionable along the paddle support structure. In yet another example, the at least one compression element has two compression elements. In still another example, each compression paddle of the two compression elements includes a compression surface, wherein each compression element is configured to orient the compression surfaces in a first position wherein the compression surfaces are substantially parallel and a second position where the compression surfaces are substantially coplanar.

In another example of the above aspect, a first one of the two compression elements is configured to move towards and away from a second one of the two compression elements. In an example, the at least one compression paddle has a compression surface and an opposite surface, and wherein the transducer is disposed in contact with the opposite surface. In another example, the breast ultrasound imaging system further includes a paddle support structure motor for rotating the paddle support structure relative to the arm axis, wherein the motor is disposed in at least one of the gantry and the paddle support structure. In yet another example, the ultrasound transducer includes two ultrasound transducers, wherein each ultrasound transducer is configured for movement along within the compression paddle along discrete axes.

In another aspect, the technology relates to a method of imaging a breast with an ultrasound imaging system having a first compression paddle and a second compression paddle, the method including: positioning the first compression paddle and the second compression paddle in a first position wherein a compression surface of each of the first compression paddle and the second compression paddle are disposed facing each other; compressing when in the first position, a first surface of the breast against the first compression paddle and a second surface of the breast against the second compression paddle: performing an ultrasound imaging procedure of the first surface of the breast and the second surface of the breast in the first position while the at least one breast is compressed. In an example, positioning the first compression paddle and the second compression paddle in a second position wherein the compression surface of each of the first compression paddle and the second compression paddle are disposed coplanar to each other: contacting at least one of the first compression paddle and the second compression paddle with a third surface of the breast: and performing an ultrasound imaging procedure of the third surface of the breast in the second position while the at least one breast in contacting at least one of the first compression paddle and the second compression paddle. In another example, when the first compression paddle and the second compression paddle are in the first position, orienting the first compression paddle and the second compression paddle in at least one of a first orientation, a second orientation disposed at an orthogonal angle to the first orientation, and a third orientation disposed at a non-orthogonal angle to both the first orientation and the second orientation. In yet another example, the first compression paddle and the second compression paddle are in the first position, the at least one breast includes a single breast. In still another example, the first compression paddle and the second compression paddle are in the second position, the at least one breast includes a first breast and a second breast. In another example, two surfaces of the first surface, the second surface, and the third surface at least partially overlap.

DETAILED DESCRIPTION

An upright breast ultrasound system is shown and described that provides several advantages over ultrasound systems of the prior art. The rotatable compression assembly allows ultrasound imaging of a breast from multiple positions and orientations. The pivoting compression paddles allows the system to be used for single breast scan as well as dual breast scan, depending on the size of the paddles, breast size, position, etc. Providing ultrasound transducers in each of the compression paddles enables relatively simultaneous image capture from different sides of the breast (for craniocaudal view (CC), mediolateral oblique (MLO), and lateral scans). This is particularly advantageous for larger breasts, where the sound waves may not be able to penetrate through the entire breast thickness if scanned from only a single side. In the case of a frontal scan, two different breasts may be scanned simultaneously, also improving workflow times. The material of the patient surface of the paddle stabilizes the breast with minimal patient discomfort, while providing a smooth surface along which the ultrasound transducer can glide during the scan of the breast. By securing the breast for ultrasound imaging, movement of tissue is reduced, thus allowing for improved imaging. A user interface mounted on the gantry allows a user to customize their scan workflow.

Figure 1:
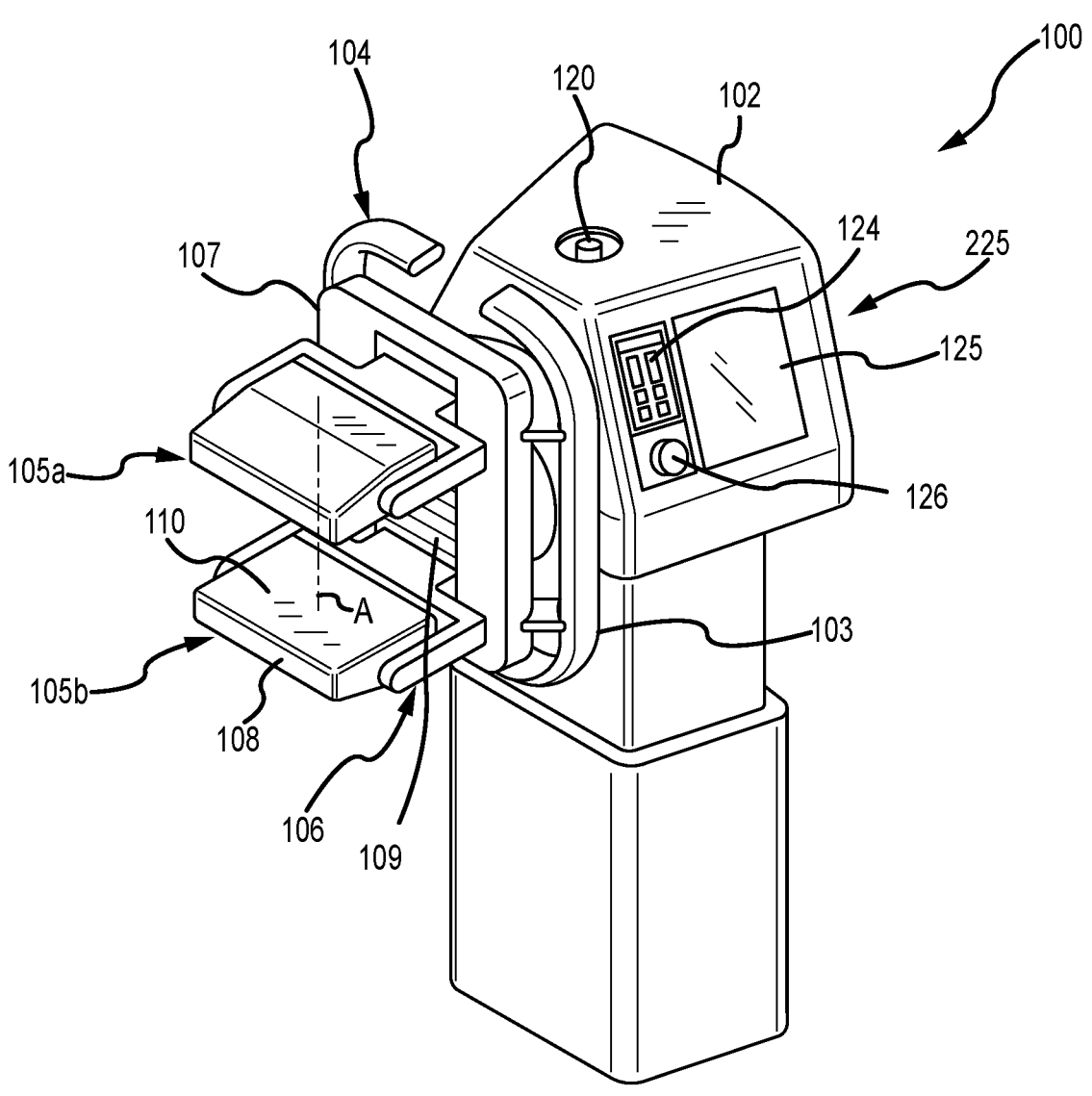
FIG. 1 illustrates one embodiment of an upright breast ultrasound imaging system of the present technology, with compression paddles in a first position and first orientation.
Figure 2:
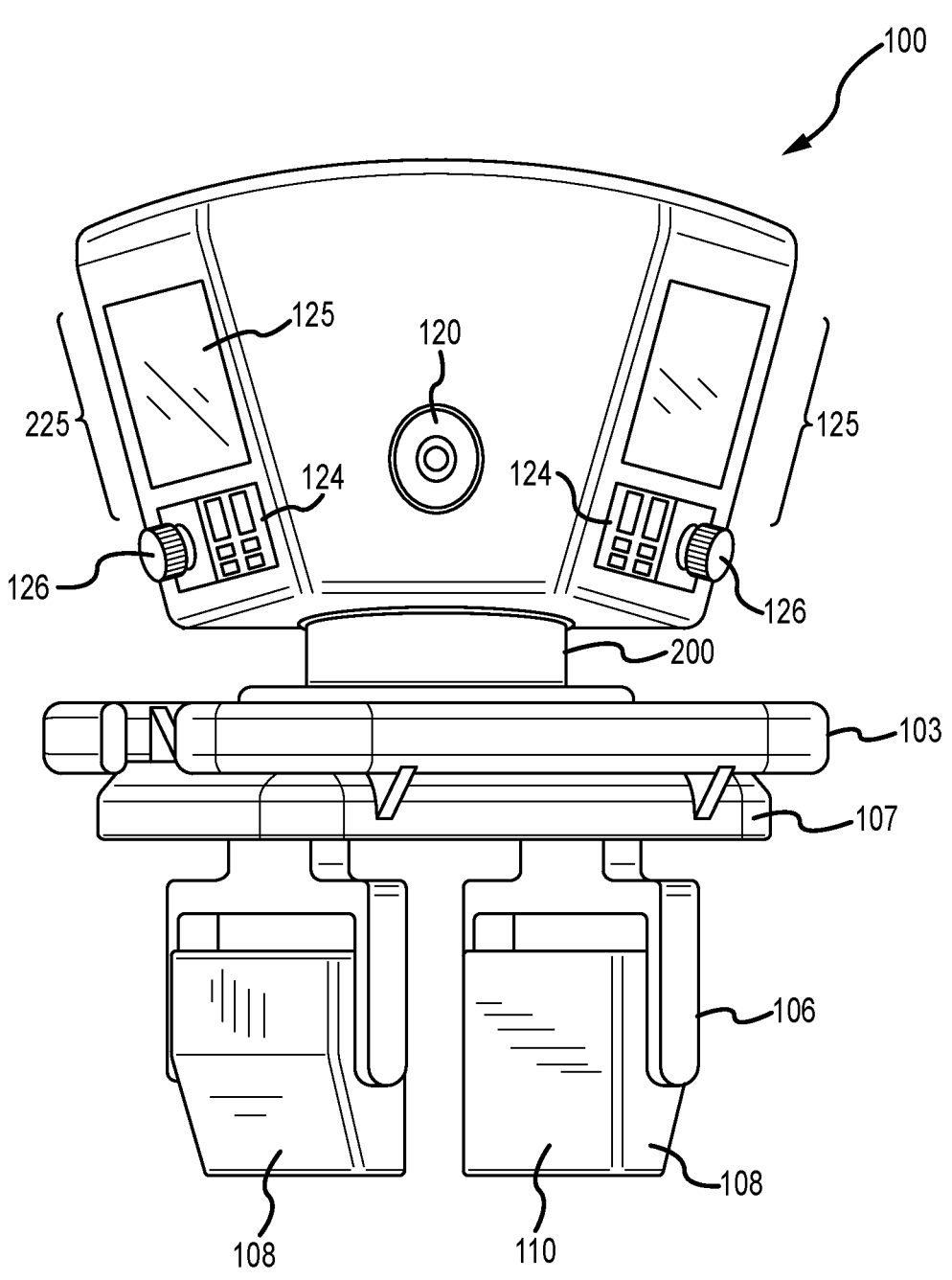
FIG. 2 is a top schematic view of the imaging system of FIG. 1 with the compression paddles in a first position and a second orientation.
Figure 3:
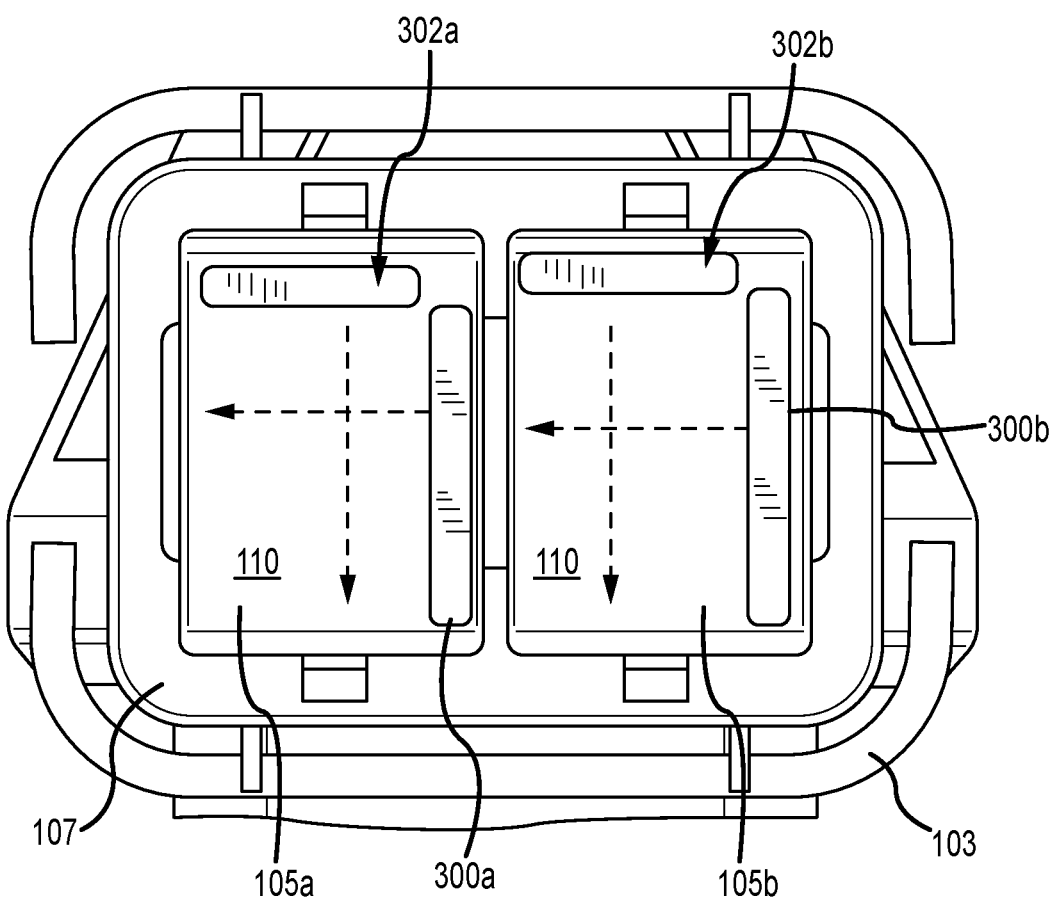
FIG. 3 is a partial front view of the imaging system of FIG. 1 with the compression paddles in a second position.

FIGS. 1-3 illustrate an exemplary embodiment of an upright ultrasound breast imaging device 100 of the present technology in various positions and orientations. The imaging device includes a gantry 102 coupled to a compression assembly 104 via a rotatable support arm 200 (FIG. 2). The compression assembly 104 includes a pair of generally parallel disposed compression paddles or elements 105a and 105b mounted on a paddle support and control structure 107. Each compression paddle 105a, 105b includes a housing 108 containing one or more ultrasound transducers 300a, 300b, 302a, 302b (FIG. 3). The housing 108 is generally parallelepiped in shape and includes a patient contact surface 110. The housing 108 may be composed of a rigid material such as plastic and the like. In various examples, the patient contact surface 110 may be removed from the housing 108 for cleaning and/or disposal.

The patient contact surface 110 may be a non-rigid compression material or a rigid compression material, as required or desired for a particular application. If a flexible material, the compression material may be stretched over a frame of the housing 108, for example, at an outer edge thereof. Examples of elastic materials include, for example, an elastic or substantially elastic material such as a flex plastic or mesh material, nylon, lycra, and the like. In alternate examples, the compression material may be made of a texturably couplant porous material sheet as described in WO2007/014292 assigned to U-Systems, Inc., the disclosure of which is hereby incorporated by reference herein in its entirety. In the case of rigid materials, the compression material may be a rigid plastic such as TPX™ polymethylpentene polymer. In general, it is desirable that any compression materials utilized transfer sound waves in a manner similar to human breast tissue. As such, other materials meeting such performance metrics are contemplated. If rigid materials are utilized, it may be desirable for the patient contact surfaces 110 thereof to be to be striated, grooved, or otherwise textured, so as to resist undesirable movement of breast tissue when the breast is compressed in the compression assembly 104. Movement thereof may be caused by sweat, coupling gel required for ultrasound imaging, or a combination thereof.

The compression paddles 105a, 105b are pivotably mounted on the paddle support and control structure 107 via paddle support arms 106. According to one aspect, the compression paddles 105a, 105b may be pivoted on the paddle support arms 106 through at least two secured positions: a first position wherein the patient contact surfaces 110 of the paddles 105a. 105b of the compression assembly 104 face each other (e.g., FIGS. 1 and 2), and a second position wherein the patient contact surfaces 110 are disposed so as to be generally coplanar (e.g., FIG. 3). In the first position, the compression paddles 105*a*, 105*b* may be disposed in a number of orientations, for example, wherein an axis A extending generally orthogonally to both patient contacting surfaces 110 may be disposed parallel to the horizontal, orthogonal to the horizontal, or at an angle to the horizontal. These orientations are described in further detail below and correspond generally to ultrasound images obtained for lateral scans, cranial caudal (CC) scans, and mediolateral oblique (MLO) scans, respectively. In the second position, ultrasound images of the breast can be obtained using a frontal scan. In examples, when in the first position, typically only a single breast is compressed between the paddles 105*a*, 105*b* at a time for imaging. In the second position, both breasts may be imaged substantially simultaneously (e.g., one breast in contact with each patient contact surface 110. More detail regarding the various types of scans enabled by this invention will be described with regards to FIGS. 5A and 7E. Additionally, in the first position, transducers in each compression paddle 105*a* 105*b* may scan opposite sides of a breast substantially simultaneously.

The paddle support and control structure 107 includes a track 109, on which the compression paddles 105*a*, 105*b* are mounted and a motor (not shown) for moving the compression paddles 105*a*, 105*b* along the track 109. More specifically, the paddle support arms 106 are moved by the motors. In various examples the movement of the compression paddles 105*a*. 105*b* may be coordinated (e.g., substantially simultaneous in rate while opposite in direction), such that they both move towards and away from each other relative to a common datum disposed therebetween. Alternatively, the positions of the compression paddles 105*a*. 105*b* may be independently controlled, such that one compression paddle moves while the other compression paddle remains fixed. For CC, MLO, and lateral scans, the compression paddles 105*a*, 105*b* are typically advanced towards each other so that patient contact surfaces 110 of the paddles contact opposite surfaces of a patient's breast. In another example, movement of the compression paddles 105*a*, 105*b* may be coordinated until the breast is contacted by one of the compression paddles 105*a*, 105*b*. Thereafter, the other compression paddle may be moved until the desired compression is attained, while the first paddle remains fixed in position. This may be especially desirable in the CC scan position, for example, so as to more easily accommodate patients of different heights without unnecessarily lifting the breast up or pushing the breast down.

The degree of contact between the breast and the paddles should be sufficient to stabilize and hold the breast yet need not fully compress the breast, as is typical for other imaging modalities such as mammography and tomosynthesis. Regardless, some compression of the breast invariably occurs: as such, the term "compression" is used primarily within. For frontal scans, the compression paddles 105*a*, 105*b* are rotated towards the patient, and moved towards locations which generally center the paddle at the patient's nipple or otherwise move the paddles to close proximity to capture both breasts. One aspect of the present technology is the capability of the system to quickly obtain an ultrasound scan of both breasts using the frontal scan without patient repositioning. Given contact between the breast and the patient contact surfaces 110 is required for proper imaging, it is contemplated that, depending on breast size, breast density, degree of compression, and other factors, a complete ultrasound imaging procedure of the breast may be performed in a scanning in a single configuration (e.g., for small breasts), or in two or three configurations (e.g., for larger breasts). At least one benefit of the technology described herein relates to the ability of a technician to adjust the system 100 quickly between the various positions and orientations so as to improve workflow.

The compression assembly 104 also includes positioning handles 103 coupled to the paddle support and control structure 107. The positioning handles 103 may be used to manually rotate the compression assembly 104 to various positions relative to the gantry 102 to enable breast imaging in multiple different perspectives. In the case of this manual rotation, a locking mechanism between the rotating arm 200 and the compression assembly 104 secures the assembly 104 in any one of a variety of positions as described elsewhere herein. For example, FIG. 1 illustrates the compression assembly positioned in a CC position which is regularly used for breast imaging. In another example, a motor (not shown, but disposed within the gantry 102) may be used to rotate the paddle support and control structure 107 based user input controls. In this example, the positioning handles 103 may still be utilized so as to provide a location for the patient to grip for greater comfort or support during procedures. In either the manual- or motorized-rotation examples, an interlock that prevents rotation of the paddle support and control structure 107 when pressure above a certain threshold is applied to both paddles 105*a*, 105*b* may be utilized to prevent inadvertent rotation of the paddle support and control structure 107 when a breast is compressed. Such an interlock may include a strain gauge or other types of sensors on each of the support arms 106.

The gantry 102 includes at least one user interface 225 including control buttons and knobs that may be used to control various aspects of the imaging system 100 including but not limited to movement of the compression assembly 104, paddle support and control structure 107, paddles 105*a*, 105*b*, and transducer. The interface 225 also may include a display 125 and/or touch screen that allows a user to select certain views, initiate scan sequences, move components of the system, etc. It is appreciated that various control mechanisms may be manifested by different features, and no limitation is placed on the form or function of the interface 225.

FIG. 2 is a top view of the breast imaging system 100 of FIG. 1. In this example, two user interfaces 225 are advantageously provided on the gantry 102, allowing a user to access the patient from either side of the system 100. The user interfaces 225 may include a graphic user interface (e.g., in the form of a touch screen 125), and one or more tactile features in the form of buttons 124, knobs 126, switches, etc. In addition, a shutdown or release switch 120 is provided on the top of the device, providing a mechanism for the technician to quickly release the breast from compression, while limiting the potential that the release switch 120 is inadvertently activated via the user interface 225. In the top view of FIG. 2, the compression assembly 104 is shown in a MLO position for ultrasound image acquisition.

FIG. 3 illustrates a perspective view of the compression assembly 104 of the breast imaging system of FIG. 1. In FIG. 3, the compression paddles 105*a*, 105*b* have been rotated into a second position so that the patient contact surface 110 faces the patient for a frontal scan. In such frontal scans, the patient may lean into the compression paddles 105*a*. 105*b* from a seated or standing position. In FIG. 3, the patient contact surface is depicted as transparent for ease of view of the transducers. FIG. 3 shows a pair of transducers 300*a*, 302*a*, 300*b*, 302*b* in each compression paddle 105*a*, 105*b*. A vertical scan transducer 302*a*, 302*b* and a horizontal scan transducer 300*a*, 300*b* are disposed in each compression paddle 105*a*, 105*b*. The transducers 300*a*, 302*a*, 300*b*, 302*b* are coupled to a scanning arm (not shown) which controls the speed of and path taken by the transducer 300*a*, 302*a*, 300*b*, 302*b* during its scan. The scanning arm controls movement of the transducers 300*a*, 300*b* in the x direction (as depicted in FIG. 3), and transducers 302*a*, 302*b* in the y direction. This enables scanning of the full contour of the immobilized breast in as little as a single scan (depending on breast size and position, transducer size, etc.). The two transducers 300*a*, 302*a*, 300*b*, 302*b* are positioned so as to not interfere with each other's scan. Indeed, by using two transducers located on opposite sides of the breast (in certain orientations) a 3D reconstruction of the breast may be generated, with features detected in the opposing scans being identified as matching pairs. The opposing scans may then be combined, using the matching pairs of features as points of alignment between the two scans. It should be noted that the present technology envisions other transducer arrangements, for example different numbers and configurations of transducers. In addition, although a simple vertical and horizontal scan path is shown, other scan paths, including a helical scan path or the like, could be substituted readily herein by one of skill in the art. In such a configuration, it may be advantageous to utilize transducers having smaller dimensions. The transducer scanning arm also controls the speed with which the transducer scans the breast. In various embodiments, the speed may be constant, may vary depending upon breast characteristics (such as size, density, regions of interest, or patient age), or may be manually controlled.

Figure 4:
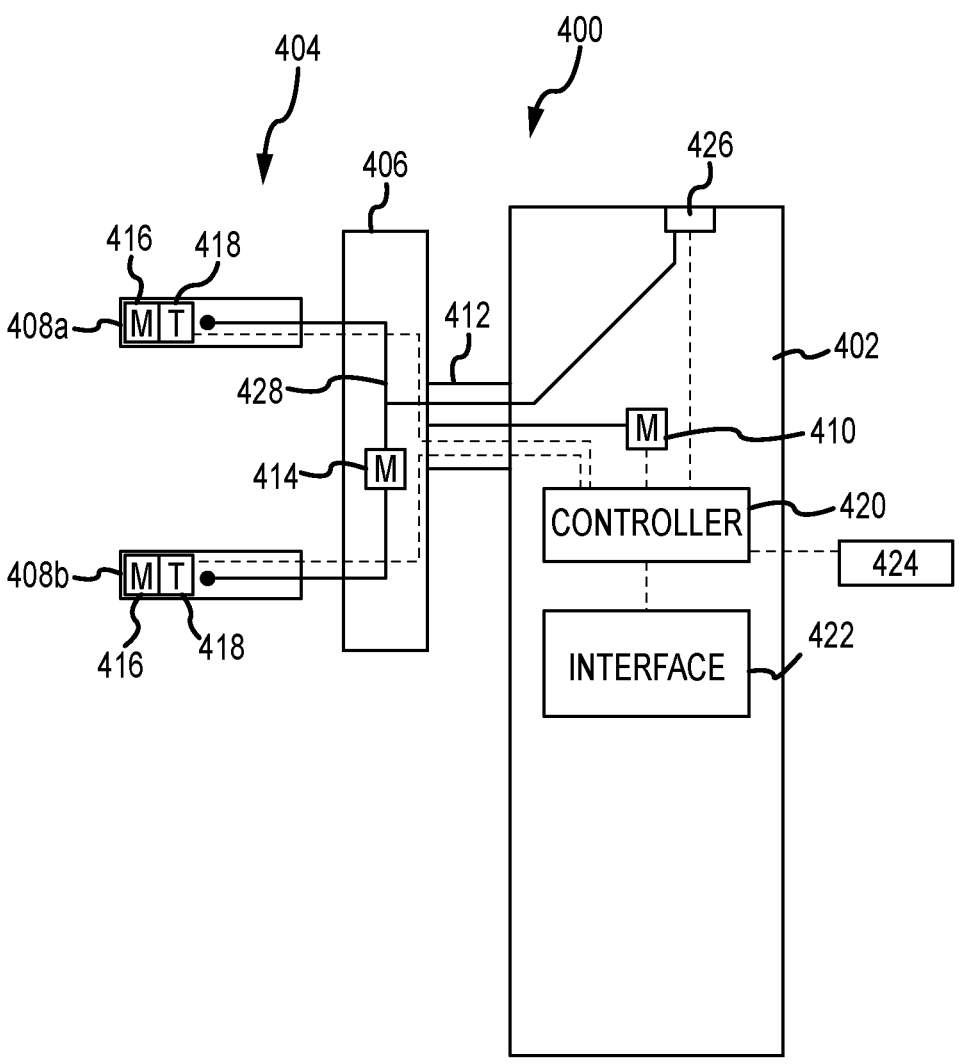
FIG. 4 is a schematic view of an ultrasound imaging system.

FIG. 4 is a schematic view of an ultrasound imaging system 400 that includes a gantry 402 and a compression system 404 that includes a paddle support and control structure 406 and a pair of compression paddles 408*a*, 408*b*. The gantry 402 includes a paddle support motor 410 for rotating the paddle support and control structure 406 at the end of an arm 412. An additional paddle motor 414 may be utilized to move at least one of the paddles 408*a*, 408*b* towards and away from the other paddle 408*a*, 408*b*. Last, at least one motor 416 may be disposed in each paddle 408*a*, 408*b* and be configured to move a transducer 418. Multiple transducers 418 in each paddle 408*a*, 408*b* may require multiple motors 416. Each of the various motors 410, 414, 416, as well as the transducers 418 may be controlled by one or more controllers 420 disposed in the gantry 402. A user may program, control, or otherwise operate the controller 420 from an interface 422, such as the user interface(s) described above. A remote interface 424 in the form of a standalone computer may be utilized alternatively or additionally. In examples, the standalone computer may also include software required to act as a remote controller, thus obviating the need for the depicted controller 420 disposed in the gantry 402. A shutdown or release switch 426 may also be included. The release switch may be communicatively coupled to the controller(s) 420, 424 such that activation thereof automatically controls the motor 414 so as to move the paddles 408*a*, 408*b* away from each other so as to release the breast. In another example, the release switch 426 may be mechanically coupled to a component of a compression track or mechanism 428 that moves the paddles 408*a*, 408*b*. In such a configuration, the release switch 426 may serve as a mechanical release of the mechanism 428, which can release the breast from compression in the event of a power failure or software error.

Figures 5A, 5B, 5C, 5D:
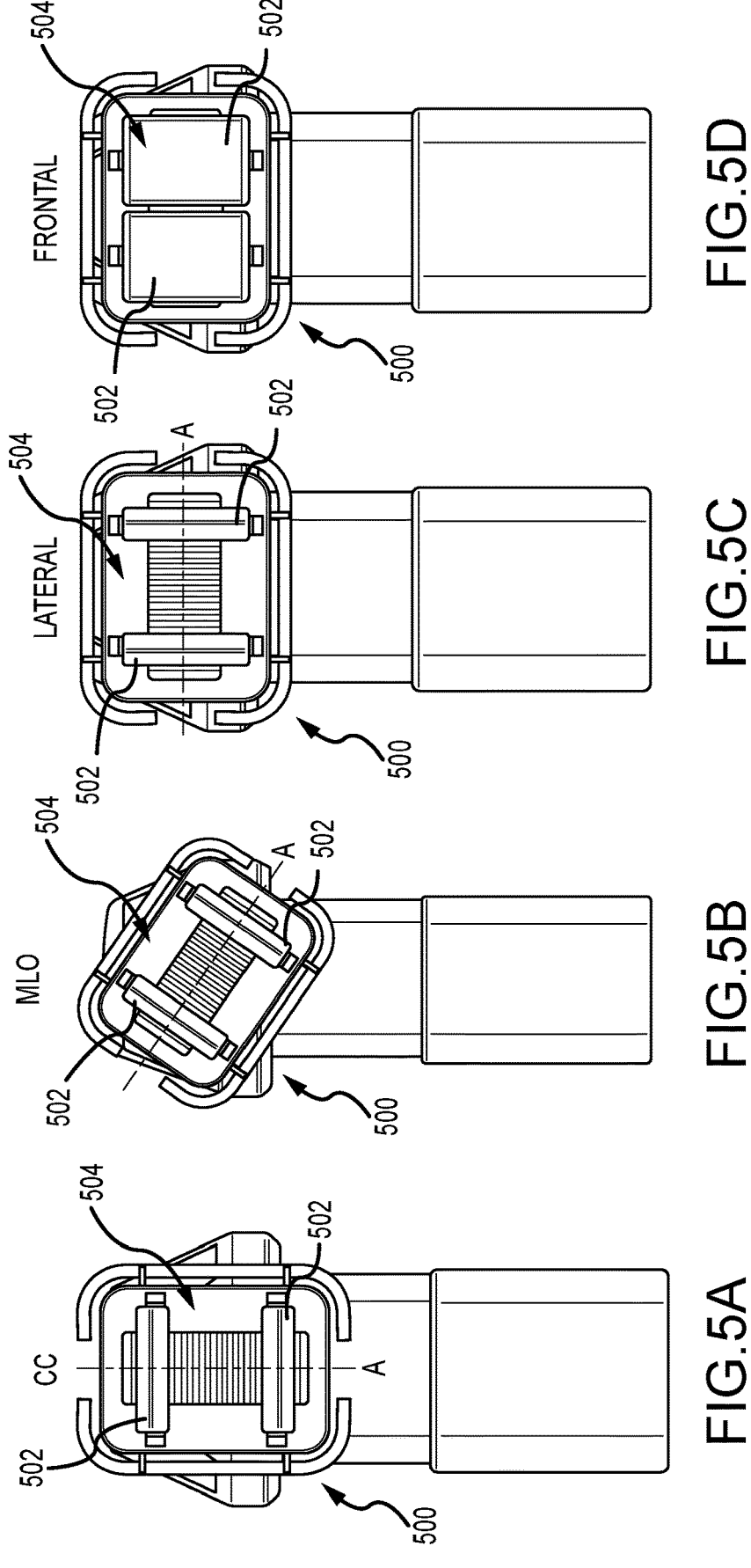
FIGS. 5A-5D are front views illustrating the ultrasound imaging system with the compression assembly positioned and oriented for breast scans at different aspects.
Figure 6A:
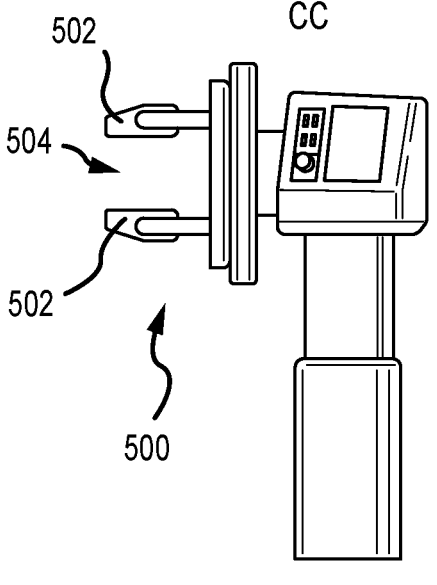
FIGS. 6A-6D are perspective views of the breast ultrasound imaging system depicted in FIGS. 5A-5D.
Figure 6B:
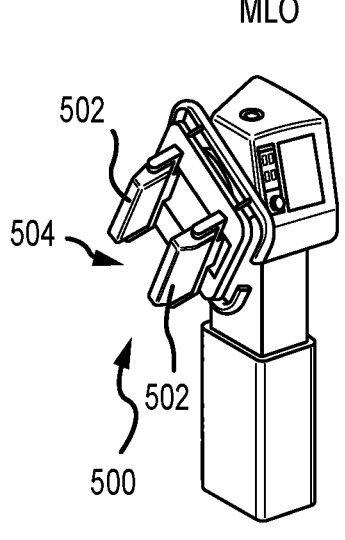
Figure 6C:
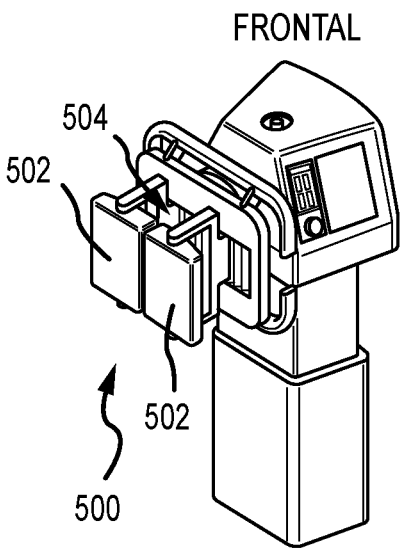
Figure 6D:
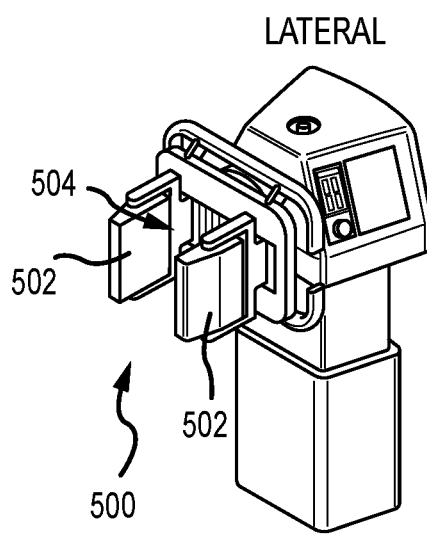

FIGS. 5A-5D are front views illustrating the breast ultrasound imaging system 500 with the compression assembly oriented for breast scans at different aspects. FIGS. 6A-6D are perspective views of the breast ultrasound imaging system 500. FIGS. 5A and 6A depict the system 500 with the compression paddles 502 in a first position, where the contact surfaces 504 thereof are disposed so as to face each other. An axis A that extends substantially orthogonally to the contact surfaces 504 is also depicted. In FIGS. 5A and 6A, the axis A is disposed substantially orthogonal to the horizontal. In this configuration, the paddles 502 are disposed in a first orientation consistent with a CC scan, where the lower of the two compression paddles 502 is utilized to support the breast. Either or both of the compression paddles 502 may be moved towards the other, so as to compress the breast therebetween for ultrasound imaging. FIGS. 5B and 6B depict the system 500 with the compression paddles 502 again facing each other in the first position. The axis A extends substantially orthogonally to the contact surfaces 504 and is depicted disposed at an angle to both the horizontal and the vertical. As such, the paddles 502 are in a second orientation consistent with an MLO scan. FIGS. 5C and 6C depict the system 500 with the compression paddles 502 again facing each other in the first position. The axis A extends substantially orthogonally to the contact surfaces 504 and is depicted disposed at an angle substantially parallel to the horizontal. As such, the paddles 502 are in a third orientation consistent with a lateral scan. FIGS. 5D and 6D depict the system 500 with the compression paddles 502 in a second position such that the contact surfaces 504 are substantially coplanar with each other. In this position, an axis orthogonal to each contact surface 504 extends substantially parallel to each other. These axes would also be parallel to the horizontal. As such, the paddles 502 are in a position consistent with a frontal scan.

FIGS. 7A-7D depict a breast 600 and identifies a plurality of areas 602 scanned during the various scans with the ultrasound imaging system described herein. The ultrasound imaging systems described herein may be used to perform one or more scans of a breast. As noted above, the size of the breast, size of the compression paddles, depth of penetration of the ultrasound signals, and other factors, may dictate the number of scans required to completely image the breast. As with other ultrasound systems, the depth of penetration of the ultrasound waves may be adjusted as required or desired for a particular application. Similarly, beam forming may be used to direct the ultrasound waves in various directions relative to the transducer, so as to increase the imaging area within the breast tissue. With these and other considerations in mind, the areas depicted within FIGS. 7A-7D show the areas along which scanning transducers may image the breast in a single pass, specifically areas of the breast in contact with the patient contact surfaces of the compression paddles during compression. The depth of penetration of the sound waves are not depicted and for the purposes of illustration, it is assumed that the sound wave penetration is in a direction orthogonal to the patient contact surfaces. In other examples, ultrasound devices that utilize phased arrays may be employed. With such phased array devices, the ultrasound waves may be steered within the breast tissue, which would enable the systems described herein to image portions of the breast not directly in contact with the compression surfaces.

Figure 7A:
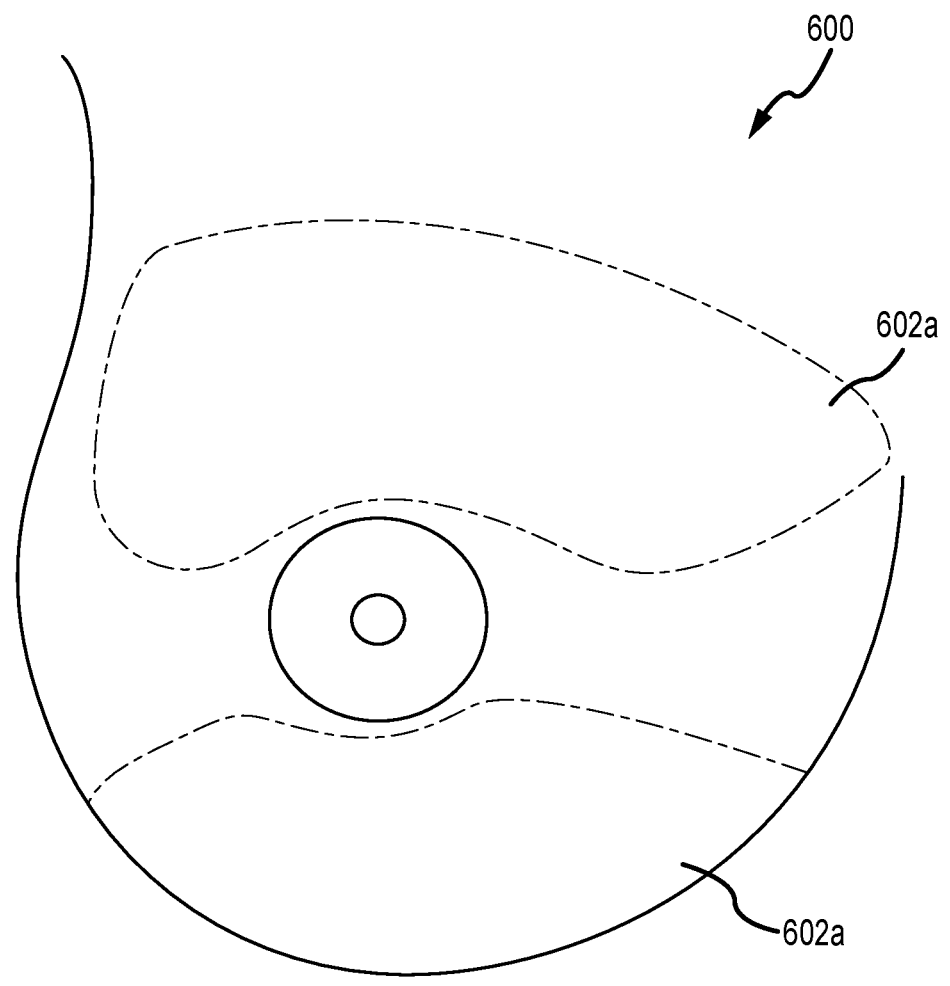
FIGS. 7A-7D depict a breast and areas scanned during various scans with the ultrasound imaging system described herein.
Figure 7B:
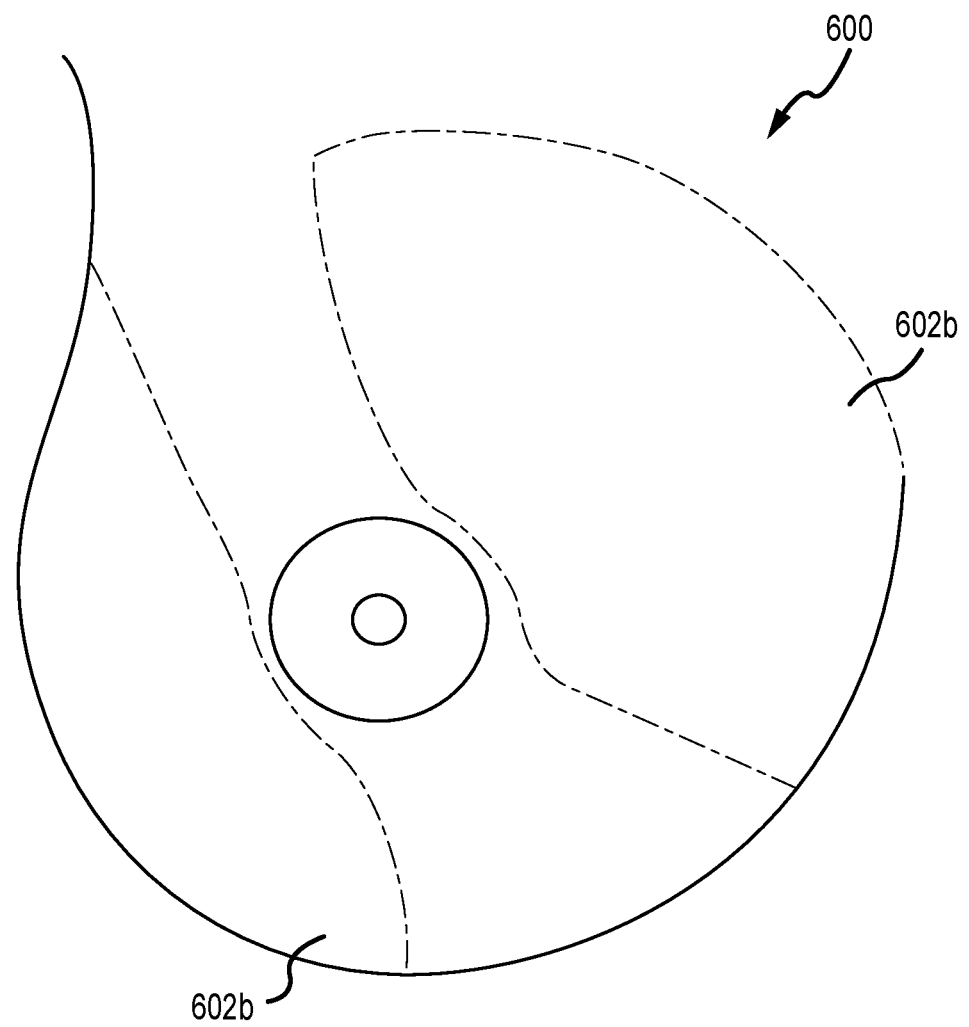
Figure 7C:
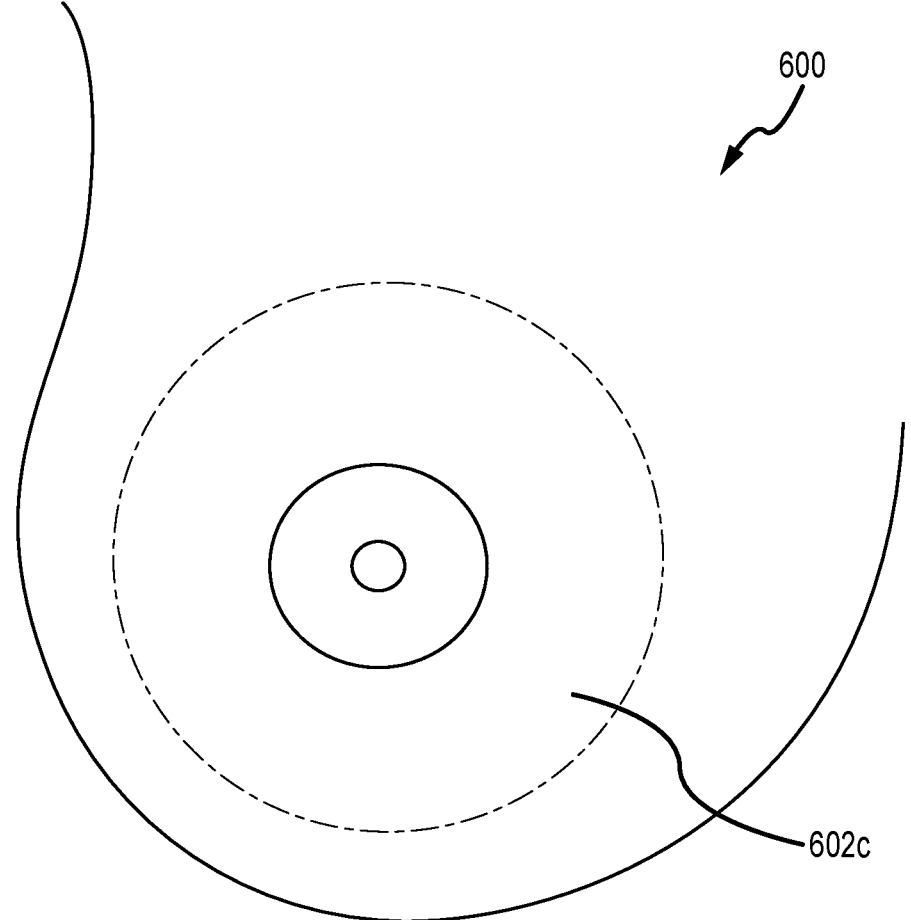
Figure 7D:
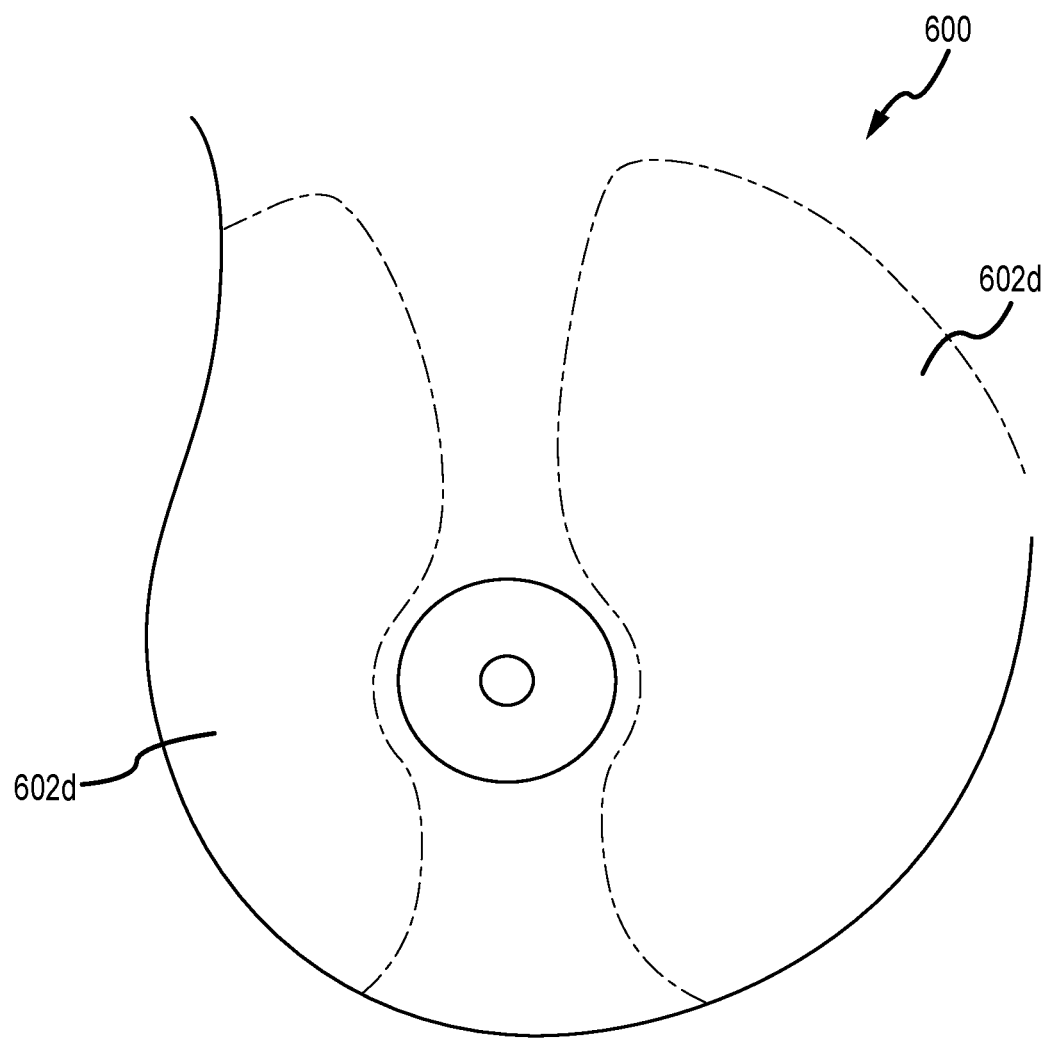
Figure 7E:
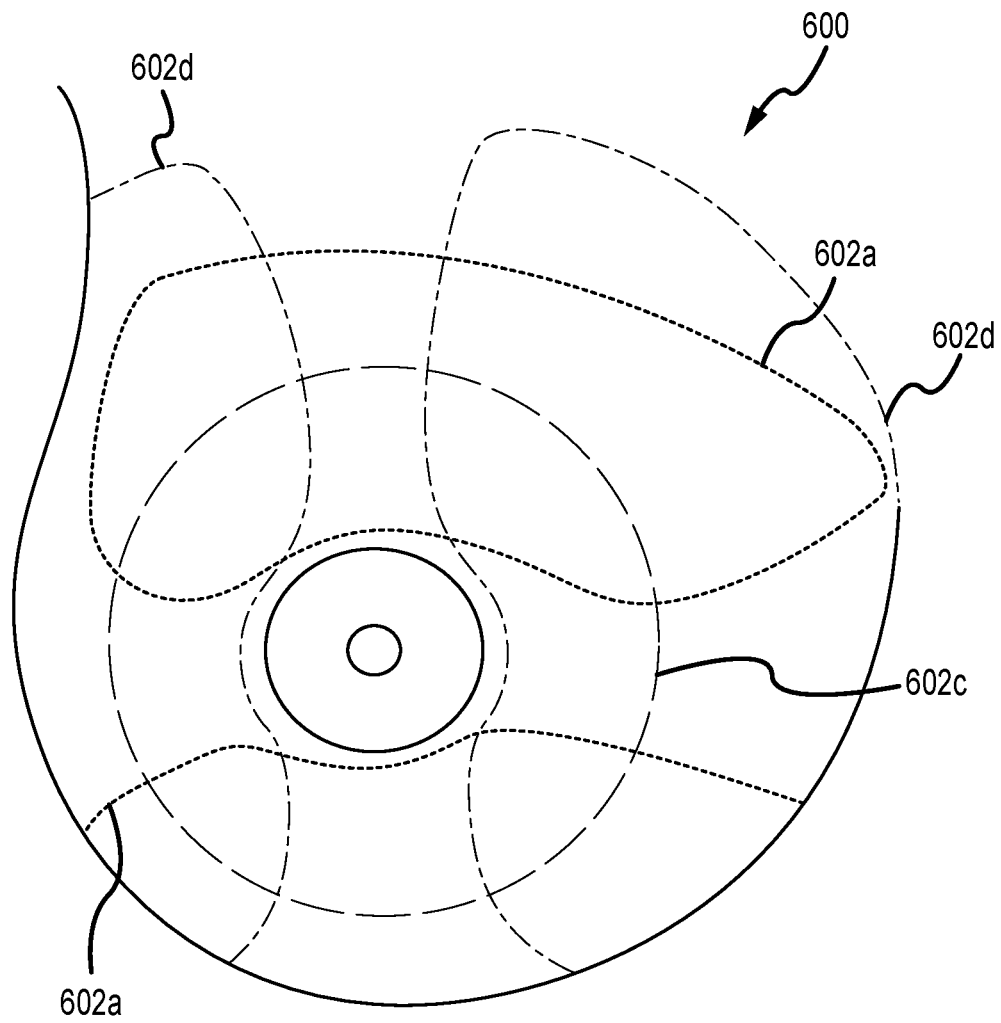
FIG. 7E depicts the breast and an overlay of a plurality of scan areas.

As such, FIG. 7A depicts the scan areas 602*a* when the breast 600 is in a CC scan configuration within the ultrasound imaging system described herein. FIG. 7B depicts the scan areas 602*b* when the breast 600 is in an MLO scan configuration. FIG. 7C depicts the scan areas 602*c* when the breast 600 is in a frontal scan configuration. FIG. 7D depicts the scan area 602*d* when the breast 600 is in a lateral scan configuration. As noted above, depending on the depth of sound wave penetration, beam spread, breast size, angle of transducer relative to the breast, and other factors, any one of these scans may provide sufficient imaging of the breast. In other examples, however, it may be desirable to perform multiple scans in various scan configurations to completely image the breast. FIG. 7E depicts the result of such a scan, where a scan areas for CC 602*a*, frontal 602*c*, and lateral 602*d* are all performed on a single breast 600. The overlap of scan areas between the various positions enable the volume of the entire breast 600 to be scanned quickly.

The ultrasound imaging system described herein may be used generally as follows. An acoustic couplant may be applied to a breast of a patient to be imaged. Additionally, acoustic couplant is also applied to an interior surface of the compression material (if a solid rigid material is utilized). In examples, the couplant may be dispensed from a nozzle or other feature internal to the compression paddle. A medical professional selects a desired scan configuration at the user interface, causing the compression assembly to pivot into a desired position and orientation. For MLO/CC or lateral scans, the patient's breast is positioned and the medical professional controls the user interface to cause the patient contact surfaces of the compression paddles to move towards each other to immobilize the breast. For frontal scans, the patient is positioned by leaning inwards towards the paddles until the professional determines that the desired contact is achieved. The professional then initiates a scan sequence. As mentioned above, in some embodiments the professional may have the ability to select a scan path and a scan speed. Following the scan, the image is displayed (either on screen 125 or at an attached image workstation, coupled to the gantry via a wired or wireless interface as is known in the art), and the technologist can determine whether additional views are required.

Figure 8:
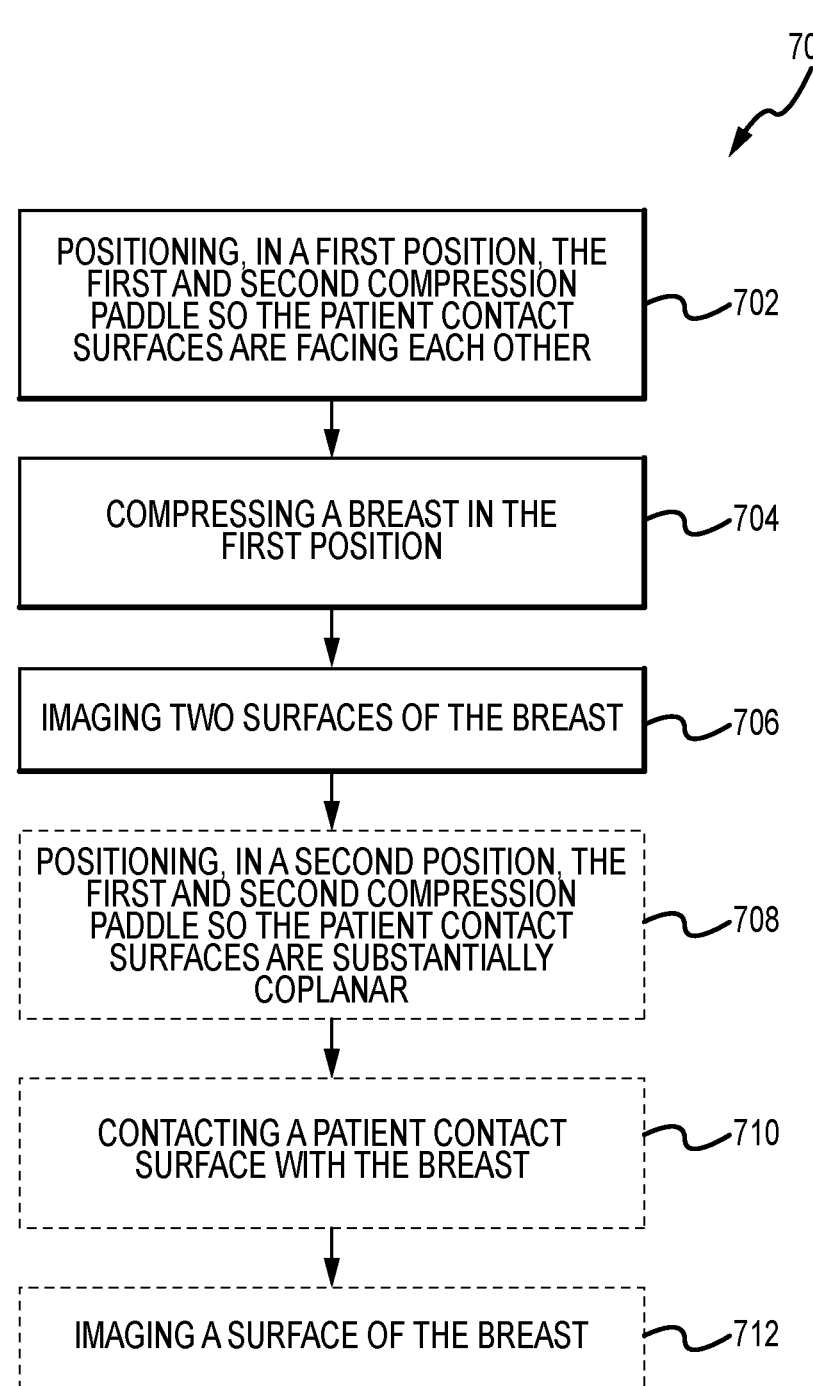
FIG. 8 depicts a method of imaging a breast with an ultrasound imaging system.

FIG. 8 depicts a method 700 of imaging a breast with an ultrasound imaging system having a first compression paddle and a second compression paddle. The method 700 includes positioning the first compression paddle and the second compression paddle in a first position, operation 702. In the first position, a compression surface or patient contact surface of each of the first compression paddle and the second compression paddle are disposed facing each other. Further, in the first position, the first compression paddle and the second compression paddle may be oriented in at least one of a first orientation, a second orientation, or a third orientation. These orientations may correspond to the CC, MLO, or lateral scan orientations described above. The method continues with operation 704, which includes compressing the at least one breast in this first position. Typically, in the first position, only a single breast is compressed and scanned, although larger paddles may accommodate two breasts in certain orientations (e.g., the CC orientation). This compressing is between the first compression paddle and the second compression paddle by placing a first surface of the breast in contact with the first compression paddle and a second surface of the breast in contact with the second compression paddle. Once compressed, operation 706 is performed. In operation 706, an ultrasound imaging procedure of the at least one breast is performed while the at least one breast is compressed in the first position. In general, this imaging procedure includes scanning opposite surfaces of a breast (each surface being in contact with a patient contact surface) substantially simultaneously with two transducers.

In other examples, only a single transducer is used adjacent a single breast surface. One or more passes of the transducer (s) may be performed, depending on the side of the breast and the size of the transducer. In optional operation 708, the first compression paddle and the second compression paddle are positioned in a second position. In this second positon, the compression surface of each of the first compression paddle and the second compression paddle are disposed substantially coplanar to each other. Once positioned, at least one of the first compression paddle and the second compression paddle is contacted with a third surface of the breast, optional operation 710. Optional operation 712 includes performing an ultrasound imaging procedure of the third surface in the second position while the at least one breast is contacting at least one of the first compression paddle and the second compression paddle. If scanning is performed with two compression paddle surfaces, both breasts may be scanned substantially simultaneously. More specifically, a first breast may be in contact with the first compression paddle, while a second breast may be in contact with the second compression paddle. Unlike operation 706, where two transducers may be utilized substantially simultaneously on the same breast, operation 712 generally requires the use of only a single transducer in each compression paddle (thus, one transducer per breast). Multiple scans by one or two transducers may be performed, however, typically only a single transducer in the associated compression paddle need be utilized. Further scans may be performed, with scan areas generally overlapping until the entire breast has been imaged.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. An ultrasound breast imaging system comprising:
a gantry; and
a compression assembly coupled to the gantry, the compression assembly comprising:
a first compression paddle and a second compression paddle each mounted on a positioning track, each of the first and second compression paddles being supported by a support arm configured to pivotably couple the respective compression paddle to the positioning track, at least one of the first and second compression paddles housing a transducer; and
at least one motor operatively coupled to both the first and second compression paddles along the positioning track for ultrasound imaging, wherein the first compression paddle is independently moveable by the at least one motor along a longitudinal direction of the positioning track relative to the second compression paddle, and wherein the second compression paddle is independently moveable by the at least one motor along the longitudinal direction of the positioning track relative to the first compression paddle;

wherein the first compression paddle and the second compression paddle are configured to be parallel to each other in a first configuration, and coplanar with each other in a second configuration.

2. The ultrasound breast imaging system of claim 1, wherein the at least one motor is configured to translate the first and second compression paddles in a coordinated manner along the positioning track.

3. The ultrasound breast imaging system of claim 2, wherein the at least one motor is configured to contemporaneously translate the first and second compression paddles.

4. The ultrasound breast imaging system of claim 2, wherein the at least one motor is configured to simultaneously translate the first and second compression paddles.

5. The ultrasound breast imaging system of claim 2, wherein the at least one motor is configured to translate the first and second compression paddles in one or more directions along the positioning track.

6. The ultrasound breast imaging system of claim 1, wherein the first and second compression paddles each comprise a patient contact surface that faces each other.

7. The ultrasound breast imaging system of claim 1, wherein the compression assembly is rotatably coupled to the gantry.

8. The ultrasound breast imaging system of claim 1, wherein the at least one motor is configured to translate the first and second compression paddles in opposite directions along the positioning track.

9. The ultrasound breast imaging system of claim 8, wherein:

the positioning track comprises a reference location therein; and the at least one motor is configured to translate the first and second compression paddles one of toward each other and away from each other with respect to the reference location along the positioning track.

10. The ultrasound breast imaging system of claim 9, wherein the reference location is a central location of the positioning track.

11. The ultrasound breast imaging system of claim 1, wherein the at least one motor is configured to control each of the first and second compression paddles both independently and contemporaneously relative to one another.

12. The ultrasound breast imaging system of claim 11, wherein the at least one motor is configured to control the plurality of compression paddles so that the first compression paddle remains fixed while the second compression paddle undergoes a translation along the positioning track.

13. The ultrasound breast imaging system of claim 1, wherein the at least one motor is configured to control each of the first and second compression paddles to translate along the positioning track until at least one of the first and second compression paddles reaches a desired location.

14. The ultrasound breast imaging system of claim 1, wherein the at least one motor is configured to control the first compression paddle and the second compression paddle to translate along the positioning track until a surface of the first compression paddle and a surface of the second compression paddle contact opposite surfaces of a breast.

15. The ultrasound breast imaging system of claim 14, wherein the at least one motor is further configured to control at least one of the first compression paddle and the second compression paddle to translate along the positioning track until a desired compression of the breast between the first compression paddle and the second compression paddle is reached.

16. The ultrasound breast imaging system of claim 15, wherein the at least one motor is further configured so that one of the first compression paddle and the second compression paddle remains fixed in place while the other of the first compression paddle and the second compression paddle translates along the positioning track.

17. The ultrasound breast imaging system of claim 1, wherein the at least one motor is configured to control the first compression paddle and the second compression paddle to translate along the positioning track until a surface of one of the first compression paddle and the second compression paddle contact a breast.

18. The ultrasound breast imaging system of claim 1, wherein at least one of the first and second compression paddles has a patient contact surface comprising a compression material.

19. The ultrasound breast imaging system of claim 1, further comprising a control structure coupled to the first and second compression paddles, the control structure comprising the positioning track and being rotatable.

* * * * *